(12) United States Patent
Hunnell et al.

(10) Patent No.: US 6,395,234 B1
(45) Date of Patent: May 28, 2002

(54) SAMPLE CASSETTE HAVING UTILITY FOR HISTOLOGICAL PROCESSING OF TISSUE SAMPLES

(75) Inventors: Jack E. Hunnell; Timothy M. McAvinney, both of Durham, NC (US)

(73) Assignee: Triangle Biomedical Sciences, Inc., Durham, NC (US)

( * ) Notice: Subject to any disclaimer, the term of this patent is extended or adjusted under 35 U.S.C. 154(b) by 0 days.

(21) Appl. No.: 09/499,890

(22) Filed: Feb. 8, 2000

(51) Int. Cl.⁷ .................................................. B01L 3/00
(52) U.S. Cl. ....................... 422/101; 422/102; 422/104; 220/831; 220/835
(58) Field of Search ................................. 422/101, 102, 422/104; 436/177; 220/4.22, 4.23, 831–836, 840, 841

(56) References Cited

U.S. PATENT DOCUMENTS

| | | | |
|---|---|---|---|
| 2,996,762 A | 8/1961 | McCormick et al. | 18/26 |
| 3,674,396 A | 7/1972 | Benjamin et al. | 425/117 |
| RE28,165 E | 9/1974 | Benjamin et al. | 425/117 |
| 3,982,862 A | 9/1976 | Pickett et al. | 425/117 |
| 4,034,884 A | 7/1977 | White | 220/8 |
| 4,220,252 A | 9/1980 | Beall et al. | 220/307 |
| 4,421,246 A | 12/1983 | Schultz et al. | 220/307 |
| 4,549,670 A | 10/1985 | Trendler | 220/338 |
| 4,752,347 A | 6/1988 | Rada | 156/382 |
| 4,801,553 A | 1/1989 | Owen et al. | 436/174 |
| 4,997,100 A | 3/1991 | Dudek | 220/306 |
| 5,061,452 A | 10/1991 | Yamamoto et al. | 422/101 |
| 5,080,869 A | 1/1992 | McCormick | 422/102 |
| 5,127,537 A | 7/1992 | Graham | 220/339 |
| 5,269,671 A | 12/1993 | McCormick | 425/117 |
| 5,358,135 A * | 10/1994 | Robbins et al. | 220/337 |
| 5,427,742 A | 6/1995 | Holland | 422/102 |
| 5,533,642 A * | 7/1996 | Lafond et al. | 220/326 |
| 5,543,114 A * | 8/1996 | Dudek | 422/102 |
| 5,968,436 A | 10/1999 | Takezaki | 264/250 |

OTHER PUBLICATIONS

"The Perfect Cassette For Your Smallest Specimens", Copyright 1997, Sakura Finetek U.S.A, Inc., Torrance, CA.

* cited by examiner

*Primary Examiner*—Matthew O. Savage
(74) *Attorney, Agent, or Firm*—Steven J. Hultquist; Marianne Fuierer; Yongzhi Yang

(57) ABSTRACT

A cassette for containment, storage and processing of material samples, having a top member that is slideably attachable to and detachable from the base member with minimal force and relaxed requirement for precision in the alignment operation. The top member is hingeably connected to the base member when attached and is positively locked to the base member in the attached closed position. The top member is easily opened and closed with one hand when attached to the base member, and facilitates high volume sample processing, e.g., of tissue samples for the purpose of histological determinations.

20 Claims, 4 Drawing Sheets

SAMPLE CASSETTE HAVING UTILITY FOR HISTOLOGICAL PROCESSING OF TISSUE SAMPLES

BACKGROUND OF THE INVENTION

1. Field of the Invention

The present invention generally relates to container devices having utility for holding samples for various procedures and uses in medical, agricultural and industrial applications, e.g., throughout processing, embedding and sectioning phases involving tissue samples for histological analysis.

2. Description of the Related Art

Processes and apparatuses for microscopically examining thin sections are well known in the art. Tissue specimens, obtained from surgical biopsies or autopsy samples, must be chemically prepared and embedded in some fixing agent, prior to being sectioned for microscopic examination. Other industrial and agricultural samples are analogously or otherwise processed for assay, analysis and quality assurance purposes. In various of these applications, it is necessary to contain the samples so that they are discretely segregated, labeled and handled during the respective steps to which the samples are subjected.

Thus, for example, tissue specimens are typically positioned in tissue cassettes prior to chemical processing. The chemical processing may include exposure to an antiseptic agent to prevent specimen degradation; exposure to alcohol or xylene to effect dehydration and removal of fat; exposure to formaldehyde for the removal of alcohol; optional staining of the sample, infiltration of the specimen with paraffin or other medium to replace any moisture chemically removed and to maintain the cellular structure intact for further examination, etc., and the tissue sample is suspended in a fixing medium that solidifies, holding the specimen in preparation for sectioning on a microtone and subsequent examination under a microscope.

The tissue cassette is a small expendable container, typically comprising a rectangular open-top base member including a bottom surface and four low walls, and a hinged, removable, or separate lid. The lid and bottom surface of the base member, and in some designs the side walls of the base member, contain numerous pores or apertures to facilitate the flow of chemicals into and out of the interior of the tissue cassette, thus contacting and processing the tissue sample contained therein. The general size and shape of tissue cassettes have been de facto standardized by the requirements of processing and cutting equipment utilized by histology and pathology laboratories, where typically over a hundred tissue cassettes containing specimens are processed simultaneously and held individually in a microtone for sectioning. Various tissue cassette designs are well known in the art.

Early designs, such as those disclosed in McCormick U.S. Pat. No. 3,674,396, were made of metal, and were expensive to manufacture. Graham U.S. Pat. No. 5,127,537 describes the advantages of plastic as a material for the manufacture of tissue cassettes, and many of its disadvantages as well, including the tendency of the tops of plastic tissue cassettes to become dislodged from the base members, due to the thin structure of the plastic hinges. Graham addresses the problem of weak plastic hinges by forming both the base member and the top as a unitary structure, connected by a "living hinge." Graham's living binge structure comprises dual thin connectors designed to be flexed many times, allowing the top to be closed on the base member by bending the connectors 180°. Graham's top element, however, when opened will assume a generally unpredictable position in relation to the base member, depending upon the elasticity remaining in the living hinge (such elasticity being a function of age, chemical exposure, and amount of previous use).

Yamamoto et al. U.S. Pat. No. 5,061,452 discloses a multi-compartment tissue cassette for the simultaneous preparation of multiple tissue samples. The Yamamoto et al. cassette employs a hinge means affixing the top to the base member similar to the "living hinge" of Graham, but extending along an entire edge of the top. The Yamamoto et al. cassette suffers the same disadvantages as the Graham cassette with respect to the positional unpredictability of top placement when open. Additionally, the Yamamoto et al. cassette is limited to small tissue samples, all of which must belong to the same patient, since it is the entire tissue cassette that is marked with an identifying number or name prior to processing of the samples. Beall et al. U.S. Pat. No. 4,220,252 discloses a tissue cassette comprising a base member and a top connected by a frangible hinge, designed to break upon either mating the top to the base member or upon disengaging the two. The top is otherwise secured to the base member, preventing disassociation during chemical processing. However, if the top is separated from the base member prior to tissue sample processing, careful manual and visual alignment of the two parts by the tissue processing clinician is necessary to engage the means of securing the two together; failure to properly align the parts may result in separation of the top from the base member during chemical processing, resulting in loss of the sample. Additionally, the separation of the top from the base member, if the cassette is opened at some point intermediate to the chemical processing, is undesirable as the top may become lost or intermixed with tops from other tissue cassettes in the same processing batch, in addition to the aforementioned problem of the subsequent precise alignment of the top with the base member to engage the means for securing the two together, as required for further processing.

Trendler U.S. Pat. No. 4,549,670 discloses a tissue cassette with a removable top portion secured to the base member by a hinge that is engaged and disengaged by elastic flexing of the hinge member. The Trendler cassette overcomes many disadvantages of tissue cassettes with frangible hinges. The Trendler hinged top design operatively couples the top to the base member throughout multiple opening/closing cycles, and does so in a manner that provides positive locking of the two sections together when in the closed position, i.e., during chemical processing of the tissue sample. The process of engaging the two parts together, however, requires application of force sufficient to elastically deform one of the structural members of the hinge. This requires that the base member be secured in a holding devise or firmly held to the work surface with one hand, while the top is held with the other hand, and sufficient force applied between the two to achieve their engagement or disengagement. In many cases, a laboratory clinician desires to hold forceps or other implement securing the tissue sample in one hand, and to manipulate the tissue cassette with the other hand. The Trendler cassette allows the top to come to rest in a predictable location when the tissue cassette is in the open position. However, this position is 180°, or "flat" against the work surface on which the base member is resting. In the open position, the Trendler cassette takes up twice as much work surface space as when closed. Also, the open top lying flat against the work surface increases the risk of contamination by contacting the top with chemicals or other substances that may reside on the work surface. Accordingly, it is desirable to provide a cassette structure that avoids such contamination of the top member of the cassette. This is achieved in other cassettes, which are openable with the top member disposed at an oblique open angle to the surface on which the cassette is reposed, but such cassettes have other deficiencies of the types described hereinabove.

McCornick U.S. Pat. No. 5,080,869 dispenses with a top altogether, and hence avoids the problems associated with a hinging mechanism or top orientation in the open position. Such cassette, however, is limited in application to use with certain tissue sample processing equipment that accepts stacked assemblies of tissue cassettes.

It would therefore be a significant advance in the field of histology to provide a tissue sample cassette that overcomes the various above-described deficiencies of the prior art.

SUMMARY OF THE INVENTION

The present invention relates in one aspect a tissue cassette including a removable, hinged top separate from the base member, whereby the top portion may be easily engaged or disengaged with the base member with one hand, without the application of undue force, and without the need for careful attention to alignment. The base member contains a guide channel and a locking chamber formed in each of its interior side walls proximate to the back wall, and the top portion contains engagement protrusions extending outwards on each side edge, proximate to the back edge, such-that the engagement protrusions of the top travel within the guide channels and into the locking chamber to attach the top to the base member. The containment of the engagement protrusions within the locking chamber when the top is in a closed position, together with latching means near the front wall of the tissue cassette, provide a positive locking action, securing the top to the base member during chemical processing, and retaining the tissue sample therein. The front latching mechanism of the cassette advantageously includes a latch hook engaging a latch landing surface along the front edge of the tissue cassette, and small hemispherical latching protrusions extending from the top edges of the top that mate with latching depressions formed in the interior side walls of the base member. In combination, the three latching means securely hold the top to the base member, while allowing the top to be easily opened with one hand.

The tissue cassette of the invention thus provides a structure including a base member and a top portion slideably attachable thereto and detachable therefrom without the application of excessive force, wherein the top portion is hingedly attached on the base member.

In such tissue cassette the hinged top is readily attachable to and detachable from the base member without deformation of or damage to the hinging mechanism. Further, the top is attachable to and detachable from the base member in a manner that is largely self-locating, and that does not require extensive mechanical and visual alignment of the parts to effect the respective coupling and decoupling operations. The hinge mechanism positively secures the top to the base member when the top is in the closed position and the top is attached to the base member. The cassette may be easily opened or closed with one hand.

The top of the tissue cassette, when in the open position, rests in a predictable and repeatable orientation that facilitates depositing tissue samples into or retrieving tissue samples from the cassette, while occupying minimal space on the work surface and minimizing the likelihood of contamination through inadvertent contact of the top with foreign substances.

In one embodiment of the invention, the base member and the top may be formed of dissimilar material, with the base member being disposable and the top reusable in character.

The tissue cassette in one embodiment comprises a front latching mechanism arranged so that deformation of the central portion of the top, e.g., by manually pressing downwardly thereon, facilitates the release of the latching mechanism to thereby open the cassette.

Other aspects, features and specific embodiments of the invention will be more fully apparent from the ensuing disclosure and appended claims.

DETAILED DESCRIPTION OF THE INVENTION AND PREFERRED EMBODIMENTS THEREOF

Figure 1:
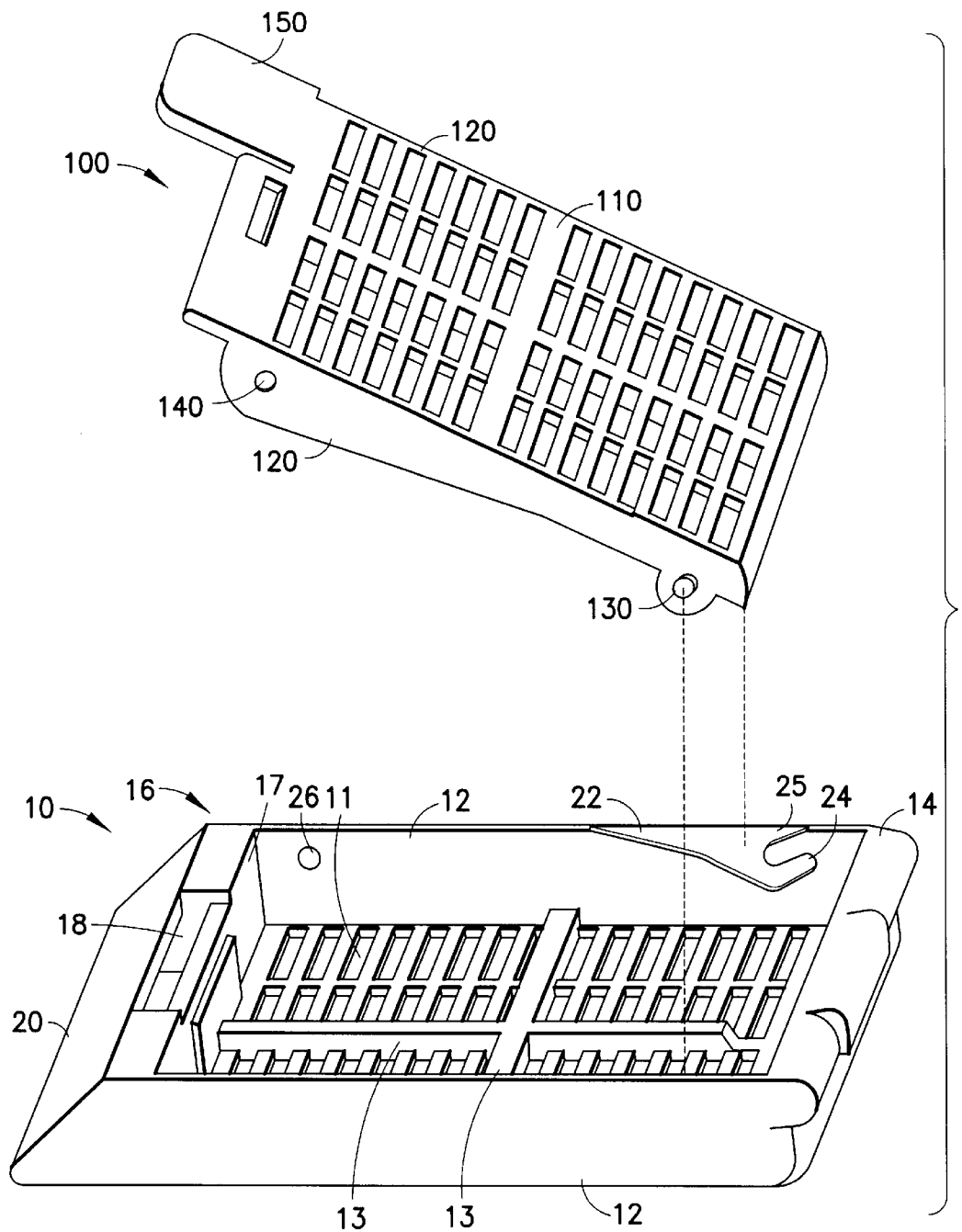
FIG. 1 is a perspective exploded view of the base member and top of a tissue cassette according to one embodiment of the present invention.
Figure 2:
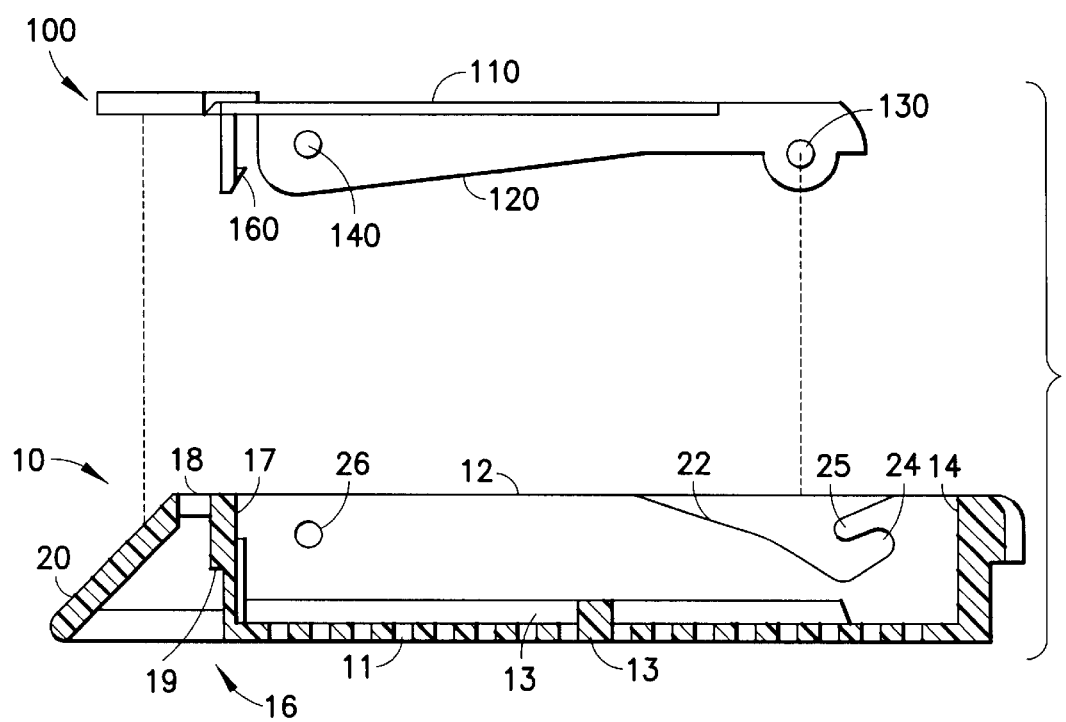
FIG. 2 is a longitudinal sectional exploded view of the base member and top of the tissue cassette of the FIG. 1 embodiment of the invention.

Referring now to the drawings, FIG. 1 is a perspective exploded view of a tissue cassette according to one embodiment of the present invention, comprising base member 10 and top 100. FIG. 2 is a longitudinal sectional exploded view of the FIG. 1 tissue cassette, wherein the features are correspondingly numbered with reference to FIG. 1, for ease of reference and description.

Base member 10 is generally rectangular in shape, and comprises a compartment for the containment of tissue samples, defined by bottom surface 11, two longitudinal side walls 12, transverse back wall 14, and transverse chamber front wall 17 of front wall assembly 16. Bottom surface 11 has a plurality of apertures formed therein to effect fluid flow through bottom surface 11. To preserve structural integrity and rigidity while providing the maximum fluid flow space through the apertures, longitudinal and transverse reinforcement members 13 are formed within bottom surface 11.

Front wall assembly 16 contains chamber front wall 17 with front latch landing 19 formed in the exterior surface thereof (see FIG. 2), front latch receiving slot 18, and marking surface 20. Marking surface 20 is a flat, oblique surface on which tissue sample identification information, such as patient names, sample numbers, or other indicia, may be printed or written. Side walls 12 each have a formed therein, on the interior face thereof and proximate to back wall 14, guide channel 22 and locking chamber 24. Guide channel 22 and locking chamber 24 are formed in side wall 12 as a partial void in the thickness of side wall 12. Locking chamber 24 is defined by locking lip 25. Side walls 12 each have also formed therein, on the interior surface thereof and proximate to the front wall 16, side latch depressions 26, formed in side wall 12 as a partial void in the thickness of side wall 12.

Top 100 is generally rectangular in shape, having an extent in the transverse dimension of slightly less than the distance separating the interior sides of side walls 12 of base member 10, and having an extent in the longitudinal dimension somewhat greater than the distance separating the interior side of back 14 and the exterior side of chamber front wall 17 of base member 10 (with finger tab 150 extending additionally over front wall assembly 16). Top 100 comprises top surface 110, top edge members 120, front latch hook 160, and finger tab 150. Top surface 110 has a plurality of apertures formed therein to effect fluid flow through top surface 110. Top edge members 120 extend downwardly in a direction perpendicular to top surface 110, and are joined to or integrally formed with the longitudinal sides of the top surface. Extending outwardly in the transverse direction from each of top edge members 120, proximate to the rear edge of top surface 110, are engagement protrusions 130. Engagement protrusions 130 are generally cylindrical in shape.

The transverse distance measured between the furthest extent of engagement protrusions 130 on each of top edge members 120 is greater than the distance between the interior faces of side walls 12 of base member 10, but less than the distance between the exterior faces of side walls 12. Extending outwardly in the transverse direction from each of top edge members 120, proximate to the front edge of top surface 110, are side latch detents 140. Side latch detents 140 are generally hemispherical in shape, and extend outwardly from top edge members 120 to a lesser extent than do engagement protrusions 130. The transverse distance measured between the furthest extent of side latch detents 140 on each of top edge members 120 is slightly greater than the distance between the interior faces of side walls 12 of base member 10.

Front latch hook 160 (see FIG. 2) is generally perpendicular to top surface 110 and is disposed at the front edge of top surface 110, centered transversely thereon and aligned with front latch slot 18 of the front wall assembly 16 of the base member 10, when the top is hingedly attached to base member 10.

Finger tab 150 is provided at the top surface 110, and extends fully over front wall assembly 16 of base member 10 in the longitudinal direction, and partially over front wall assembly 16 in the transverse direction. Finger tab 150 is disposed adjacent to one transverse edge of top 100. Finger tab 150 is of greater thickness than top surface 110, hence exhibiting a greater resilience and less deformation under a given applied force.

Figure 3:
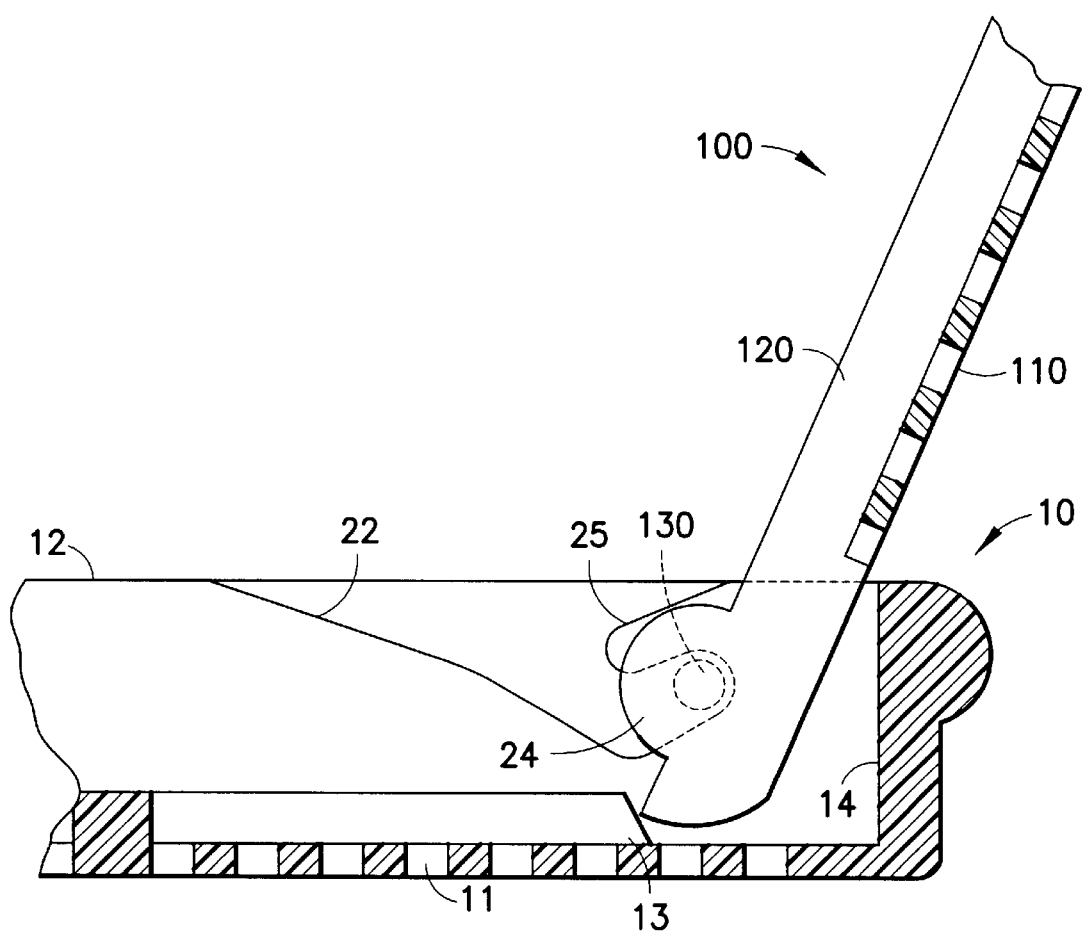
FIG. 3 is a schematic representation of a tissue cassette according to one embodiment of the invention, showing details of the hinge assembly of the cassette.
Figure 4:
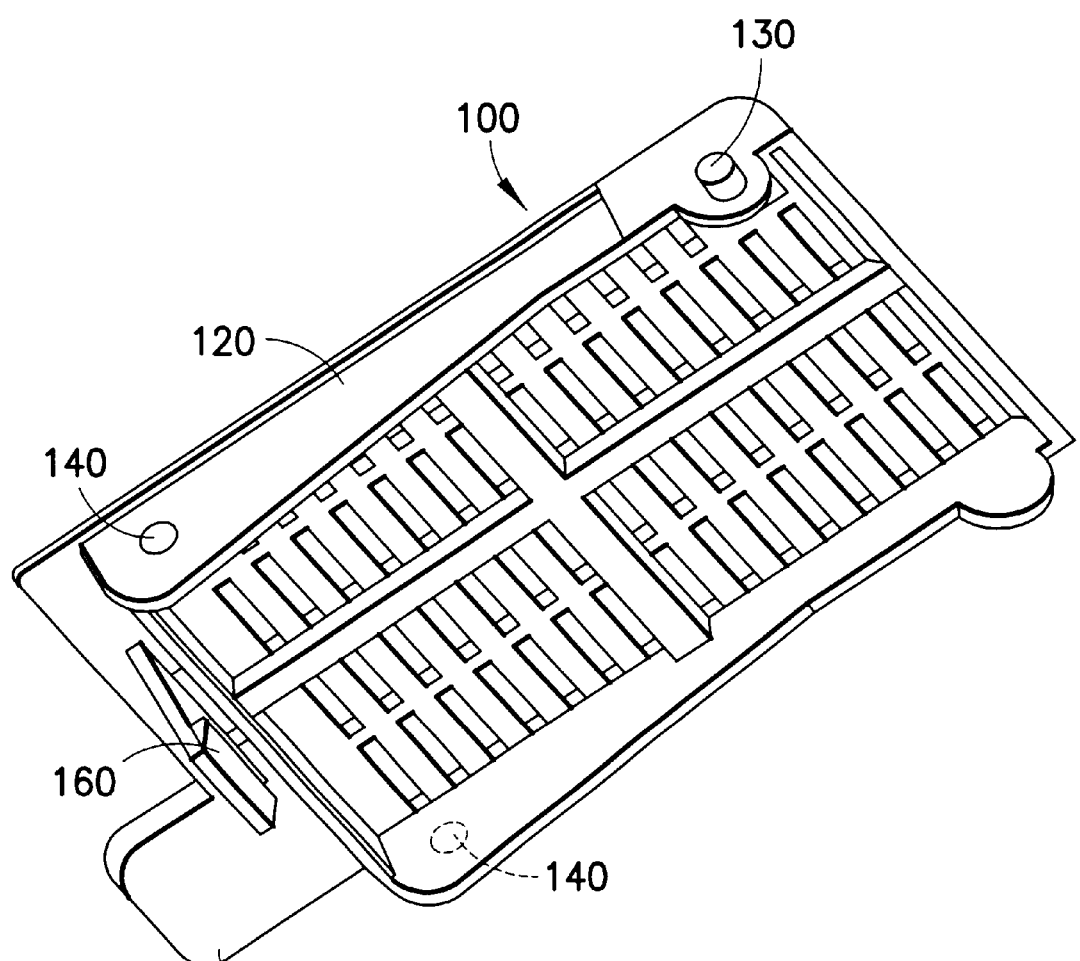
FIG. 4 is a bottom perspective view of the top of the cassette of FIGS. 1–3.

FIG. 4 is a bottom perspective view of the top 100 of the cassette of FIGS. 1–3, wherein all elements are correspondingly numbered, showing the elements of the threepoint locking system, including the two side latch detents 140 and the front latch hook 160.

The hinge mechanism of the present invention represents a significant advance over the state of the art in tissue cassette design. The top is easily attachable to and detachable from the base member, using only one hand, without requiring excessive application of force, and without the necessity of extensive mechanical and visual alignment between the two parts. The top edge members 120 of the top 100 fit within the cavity of the base member 10, between the interior surfaces of side walls 12. Engagement protrusions 130 protruding from top edge members 120 extend beyond the interior transverse dimension of the cavity of base member 10, and hence prevent the top 100 from slipping fully into the cavity. As the top 100—supported above side walls 12 by engagement protrusions 130—is translationally slid toward the rear wall 14, the engagement protrusions 130 enter guide channels 22 on the interior of side walls 12. Guide channels 22 guide engagement protrusions 130 into engagement chamber 24, beneath engagement lip 25. The top 100 is then hingedly attached to base member 10, and may be repeatedly opened and closed, pivoting about engagement protrusions 130 within engagement chamber 24.

Engagement lip 25 defining engagement chamber 24 additionally serves as a positive lock, holding the back of top 100 to base member 10 while the top is in the closed position, ie., during use of the tissue cassette in the chemical processing of tissue samples.

Disengagement of top 100 from base member 10 is equally simple, requiring no exertion of force, and capable of being performed one-handed. Top 100 is partially opened by lifting the front portion slightly away from front wall assembly 16 of base member 10.

Top 100 is then translationally slid toward the front of base member 10. Engagement protrusions 130 pass out of engagement chamber 24 by passing under engagement lip 25. Engagement protrusions 130 then slide along glide channels 22, and lift the rear end of top 100 out of the tissue chamber of base member 10, sliding along the top edge of side walls 12 after traveling the extent of glide channels 22. Top 100 is then lifted away from base member 10.

It will be appreciated from the foregoing discussion and the accompanying drawing figures that both the attachment and removal of top 100 from base member 10 are largely self-aligning processes, requiring no force. To attach the top, the clinician handling the tissue cassette need only insert the portion of top edge members 120 extending below engagement protrusions 130 into the cavity of base member 10, between the interior surfaces of side walls 12, and then gently slide top 100 toward the rear of base member 10. The top will then slide into its hingedly attached position. Removal is equally straightforward, and also requires no manual or visual alignment of parts and no application of appreciable force.

The front of top of 100 is positively latched to base member 10 by front latch hook 160 and by side latch detents 140. When the top is hingedly closed, front latch hook 160 extends through front latch slot 18 and along the exterior surface of the chamber front wall 17 in front wall assembly 16. When the top 100 is fully closed over the chamber of base member 10, front latch hook 160 engages front hook landing 19. Simultaneously, front latch detents 140, protruding from top edge members 120 of top 100, engage in front latch depressions 26 formed in the interior surface of side walls 12 of base member 10. Together, the latching mechanisms securely hold the front portion of top 100 to the front of base member 10 during use. The inherent redundancy of three separate mechanical latches in the same proximate area contributes to the security and integrity of the latching function, ensuring that tissue samples are not lost from within the chamber of the tissue cassette during chemical processing.

The front latching mechanism of the present invention also facilitates one-handed operation in unlatching and opening the tissue cassette. The engagement between the front latch hook 160 and the front hook landing 19 comprises a relatively small surface area, compared to various latches in the prior art. The front latch hook 160 thus need only move a short distance away from the exterior surface of chamber front wall 17 to disengage with the front hook landing 19 and release.

A significant feature of the design of the tissue cassette of the present invention is that by simultaneously pressing down on top surface 110, e.g. with a fingertip, and pulling up on finger tab 150, the top surface is deformed slightly inwardly into the chamber, and the front edge of top 100 is lifted upward. Front latch hook 160 is thereby pivoted outwardly away from the exterior surface of chamber front wall 17, assisting with its disengagement from front hook landing 19 and thus reducing the force necessary to effect disengagement of the front latch hook 160. Also, due to both their hemispherical shape and their slight degree of extension from top edges 120, front latch detents 140 are easily disengaged from front latch depressions 26, requiring little applied force to effect disengagement thereof.

The combination of three separate latching mechanisms, each of which individually requires relatively little force to disengage, results in secure retention of the front part of top 100 to base member 10 during use, yet allows unlatching and opening to be readily effected, using only one hand. This further contributes to ease of use of tissue cassettes of the present invention in a laboratory setting.

The cassettes of the present invention may be readily fabricated from any suitable material of construction, and are advantageously molded from plastic materials of construction. In such preferred molding fabrication of the cassette, the molds themselves may be provided with removable mold inserts to vary the structure, e.g., the size of the apertures in the top and/or base member bottom surface, to accommodate the formation of differing character cassettes for specific end usages.

Referring now to FIG. 3 (wherein corresponding elements are correspondingly numbered with respect to FIGS. 1 and 2), the position of engagement reservoirs 24 and corresponding position of engagement protrusions 130, relative to rear wall 14 of base member 10, is selected such that the top 100 comes to rest in a fully open position at an angle (measured with respect to the base member) of approximately 110°, by contacting rear wall 14. Additionally, longitudinal reinforcement element 13 does not fully extend to rear wall 14, and thereby provides an additional mechanical stop for the rear edge of top 100 in the fully open position. By maintaining top 100 in an open position suspended above the work surface, less area on the work surface is occupied by the tissue cassette during use. Additionally, inadvertent contamination of the tissue sample by chemicals or other substances on the work surface is avoided.

It will be appreciated by one of ordinary skill in the art that the utility of the present invention is not limited to the specific and illustrative embodiments disclosed in the foregoing discussion or in the appertaining drawing figures, but rather may be embodied in varied and diverse structural arrangements consistent with the requirements and limitations of the invention.

As an illustrative example, the fluid flow apertures formed in the bottom surface 11 of base member 10 and in the top surface 110 of top 100 may be of any size, shape, configuration, or arrangement that effectively facilitates fluid flow into and out of the tissue sample chamber for contact with the tissue sample therein, while preserving reasonable structural integrity and rigidity of the respective top and base member. Additionally, fluid flow apertures may advantageously be formed in the side walls 12, rear wall 14, and/or chamber front wall 17.

The positioning of the front latch hook 160, the finger tab 150, and the front latch detents 140 and corresponding front latch depressions 26 may, for example, be varied in the broad practice of the present invention. The relative demarcation of front and back as described in the present invention may be reversed, with the top 100 opening the opposite direction. The features and operations described herein could be applied to a tissue cassette hinged along the longitudinal side and opening in a transverse direction.

Although the invention has been described herein in specific reference to tissue cassette application and usage, it will be appreciated that the cassettes of the invention may be utilized generally for holding and containment of many diverse materials and samples, for correspondingly varied, industrial, agricultural and other medical applications.

The present invention extends to and encompasses other features, modifications, and alternative embodiments as will readily suggest themselves to those of ordinary skill in the art based on the disclosure and illustrative teachings herein. The claims that follow are therefore to be construed and interpreted as including all such features, modifications and alternative embodiments, within their spirit and scope.

What is claimed is:

1. A cassette having utility for holding a material sample, said cassette comprising:

a base member comprising a liquid-permeable bottom surface and a plurality of wall members defining a sample chamber for holding the sample therein, said wall members including side walls, and each of said side walls having a top edge and an inside surface;

a top member adapted to be supported on the base member and latched thereto, covering the sample chamber to retain said sample in the sample chamber when in a closed position, and a pair of protrusions extending outwardly from opposite edges of the top member, wherein the top member is slideably attachable to and detachable from the base member through a hinge mechanism at said hinged attachment, without deformation of or damage to the hinge mechanism, so that when said top member is attached to and positively locked to the base member at the point of hinged attachment, said top member and said base member are hingedly coupled to each other, wherein said hinge mechanism includes guide channels leading from the top edge of the inside surface of the side walls, and said guide channels receive said pair of protrusions; and the top member comprises a plurality of latching means at points distant to the point of hinged attachment, whereby said plurality of latching means affix the top member to the base member when in the closed position, so that the top member covers the sample chamber of the base member.

2. The cassette of claim 1, wherein said hinge mechanism comprises means for guiding the top member during its attachment to and detachment from the base member.

3. The cassette of claim 1, wherein said guide channels communicate with locking chambers defined by locking lips in said side walls, whereby said pair of protrusions are translatable through said guide channels into said locking chambers defined by said locking lips.

4. The cassette of claim 3, wherein said top member is pivotable about said pair of protrusions when said protrusions are disposed in said locking chambers defined by said locking lips.

5. The cassette of claim 1, wherein:

the base member is rectangularly shaped and comprises a bottom surface, two parallel side walls, and parallel front and back walls;

the top member is rectangularly shaped;

the hinge mechanism comprises locking chambers to which said guide channels are connected;

wherein said guide channels and locking chambers are voids on the interior surfaces of each of the two parallel side walls at a position proximate to the back wall with said voids being formed by reduction in the thickness of the two side walls, and with each of said locking chambers being defined by an overhanging engagement locking lip; and wherein said two engagement protrusions are generally cylindrical, each extending outwardly in a transverse direction from a side edge of the top member, perpendicular to the direction of the two parallel side walls, so that when the top member is reposed over the base member and translationally slid toward the back wall thereof, said engagement protrusions travel along the guide channels into the locking chambers, forming a hinged coupling about which the top member is pivotally openable and closeable over the base member.

6. The cassette of claim 5, wherein the bottom surface of said base member comprises a longitudinal reinforcement member, which does not fully extend to the back wall of the base member, thereby providing a mechanical stop for the rear edge of the top member in a fully open position.

7. The cassette of claim 6, wherein the top member is pivotally opened to a maximum extent in a fully open position, said maximum extent being characterized by an angle between the base member and the pivotally opened top member that is greater than about 90° and less than 180°.

8. The cassette of claim 7, wherein said maximum extent is characterized by an angle of about 110° between the base member and the pivotally opened top member.

9. The cassette of claim 1, wherein:
each guide channel communicates with a locking chamber defined by an overhanging locking lip; and
said guide channels and locking chambers are arranged so that said protrusions are translationally slidable along the guide channels into the locking chambers to be lockingly retained in the locking chambers, so that the top member is matably engaged with the base member.

10. The cassette of claim 1, wherein:
each guide channel communicates with a locking chamber defined by an overhanging locking lip; and
said guide channels and locking chambers are arranged so that said protrusions are translationally slidable along the guide channels into the locking chambers to be lockingly retained in the locking chambers, so that the top member is matably engaged with the base member.

11. The cassett of claim 1, wherein the latching means comprises:
a latching hook downwardly depending from an overhanging edge of the top member, and
a latching structure that is matably engageable therewith on one or more wall members of the base member,
whereby said latching hook retains the top member in a closed position over the base member by matably engaging with said latching structure, which requires an application of force to disengage said latching hook from said latching structure to open the top member from the base member.

12. The cassette of claim 11, wherein the top member is deformable, so that the force necessary to effect disengagement of the latching means and opening of the top member is reduced by the simultaneous application of a downward force directed on a central portion of the upper surface of the top member and an upward force applied to the front edge of the top member, thereby pivotally translating the latching hook away from the base member and the latching structure.

13. The cassette of claim 12, wherein the top member is made of plastic material.

14. The cassette of claim 1, further comprising means for positioning the top member above the base member in a predictable and repeatable orientation, when said top member is attached to the base member and in an open position to facilitate introducing samples into or removing samples from the sample chamber, said means comprising a longitudinal element positioned in the sample chamber to provide a mechanical stop for the top member in a fully open position.

15. The cassette of claim 1, wherein the top member and the base member are fabricated from molded plastic.

16. The cassette of claim 1, wherein the base member comprises a front wall having a face that is angled onto which sample identification information can be written and displayed.

17. The cassette of claim 1, wherein the base member and the top member are made of plastic materials.

18. The cassette of claim 1, wherein the top member and the base member have a plurality of apertures formed therein to effect fluid flow through the cassette.

19. A cassette for holding a sample, and comprising:
a base member of generally rectangular shape defining a compartment bounded by front, back, and side walls and a liquid-permeable bottom surface, with each side wall on an interior face thereof having formed therein a guide channel communicating with a locking chamber, wherein said locking chamber is bound by a locking lip; and
a cover member including engagement protrusions engageable with the guide channels of respective side walls and translatable therealong into the locking chamber to position the engagement protrusions in the respective locking chambers so that the cover member is pivotally moveable between open and closed states.

20. A cassette for holding a sample, and comprising:
a base member of generally rectangular shape defining a compartment bounded by front, back, and side walls and a liquid-permeable bottom surface, with each side wall on an interior face thereof having formed therein a guide channel communicating with a locking chamber;
said locking chamber is bound by a locking lip, with a locking slot at a front portion of the base member, and with a latch depression in each side wall at a front portion thereof;
a cover member including (a) engagement protrusions engageable with the guide channels of respective side walls and translatable therealong into the locking chambers to position the engagement protrusions in the respective locking chambers so that the cover member is pivotally moveable between open and closed states, (b) a latch hook downwardly depending at a front portion of the cover member and engageable with the locking slot on the base member, (c) downwardly extending edge members at the sides of the cover member, each having on an outside surface thereof a detent enagageable with a corresponding side wall latch depression of the base member, and (d) a frontally protruding finger tab for application of manual finger pressure in opening and closing of the cover member.

* * * * *

UNITED STATES PATENT AND TRADEMARK OFFICE
CERTIFICATE OF CORRECTION

PATENT NO. : 6,395,234 B1
DATED : May 28, 2002
INVENTOR(S) : Hunnell et al.

It is certified that error appears in the above-identified patent and that said Letters Patent is hereby corrected as shown below:

Column 1,
Line 65, "binge" should be -- hinge --

Column 3,
Line 9, McCornick" should be -- McCormick --
Line 30, "such-that" should be -- such that --

Column 6,
Line 11, "ie.," should be -- i.e., --

Column 10,
Line 6, "position" should be -- position, --

Signed and Sealed this

Twenty-ninth Day of April, 2003

JAMES E. ROGAN
*Director of the United States Patent and Trademark Office*